United States Patent [19]
Israel et al.

[11] Patent Number: 5,290,683
[45] Date of Patent: Mar. 1, 1994

[54] RAPID ANALYSIS OF ETHANOL IN BODY FLUIDS

[76] Inventors: Yedy Israel, 30 Greenfield Avenue #806, Willowdale, Ontario, Canada, M2N 3C8; Bhushan Kapur, 2374 Canso Road, Oakville, Ontario, Canada, L6J 5W6; Guang-chou Tu, 34 Lount Street, Toronto, Ontario, Canada, M4J 5A2

[21] Appl. No.: 978,534

[22] Filed: Nov. 19, 1992

[51] Int. Cl.$^5$ .................. C12Q 1/32; C12N 11/14; C12N 9/96; C12N 31/22

[52] U.S. Cl. .................................. 435/26; 435/27; 435/28; 435/184; 435/188; 435/190; 435/192; 435/176; 422/56; 422/57; 422/69

[58] Field of Search .................. 435/25, 26, 27, 28, 435/184, 188, 190, 192, 825, 174, 176, 56, 57, 69

[56] References Cited

U.S. PATENT DOCUMENTS

| | | | |
|---|---|---|---|
| 3,926,736 | 12/1975 | Bucolo | 435/25 |
| 3,992,158 | 11/1976 | Przybylowicz et al. | 435/25 |
| 4,111,751 | 9/1978 | Lange, III et al. | 435/25 |
| 4,642,286 | 2/1987 | Moldowan | 435/25 |
| 5,032,506 | 7/1991 | Palmer et al. | 435/26 |
| 5,036,000 | 7/1991 | Palmer et al. | 435/26 |
| 5,112,741 | 5/1992 | Palmer et al. | 435/25 |
| 5,141,854 | 8/1992 | Kaufman et al. | 435/26 |

FOREIGN PATENT DOCUMENTS

| | | |
|---|---|---|
| 1221008 | 4/1987 | Canada . |
| 237223 | 2/1986 | Fed. Rep. of Germany . |
| 256196 | 2/1988 | Fed. Rep. of Germany . |

OTHER PUBLICATIONS

"Early Identification of Alcohol Abuse", Proceedings of a Workshop Oct. 31–Nov. 1, 1983 by Kapur & Israel, pp. 310–320.

Janssen et al. *Biochimica et Biophysica Acta*, 1968 vol. 151, pp. 330–342.

Majkic-Singh *Analytica Chimica Acta*, vol. 115, pp. 401–405.

*Primary Examiner*—James C. Housel
*Assistant Examiner*—N. Bhat
*Attorney, Agent, or Firm*—Jeffrey T. Imai; Arne I. Fors; D. Doak Horne

[57] ABSTRACT

An assay for directly and rapidly determining the alcohol concentration of a lower alcohol in a biological fluid without dilution, comprises a solid carrier. The carrier is impregnated with a solution having the following constituents mixed in effective amounts: a cross-linked stabilized enzyme for oxidizing the alcohol in the presence of a reducible compound to produce a corresponding aldehyde and a reduction product, a chromogen which reacts with the reduction product in the presence of an agent to produce a colored compound indicative of alcohol presence in the biological fluid, a competitive inhibitor of the enzyme, an agent for converting the chromogen to the colored compound, and a buffer to maintain the solution at a predetermined acidic pH.

11 Claims, 4 Drawing Sheets

RAPID ANALYSIS OF ETHANOL IN BODY FLUIDS

This invention relates to a quantitative and qualitative determination of ethanol in biological fluids such as urine, saliva, serum or whole blood.

BACKGROUND OF INVENTION

The effect of alcohol on human beings is a significant problem from both a social and medical viewpoint. The consequences of the impaired behaviour of vehicle operators and of persons who consume excessive amounts of alcohol is increasingly being recognised as anti-social behaviour. Both for medical and social purposes it is important to obtain a fast accurate assay of the body alcohol level in a patient.

There is much need for a rapid non-invasive method to assess alcohol levels in individuals. Such a test should require no specialized training or instrumentation. A test for saliva is needed by emergency room personnel to determine if a certain level of consciousness impairment is related to alcohol intoxication or likely to other causes that may need immediate medical intervention. A test of alcohol in urine would also be of value in the physicians office, either for screening or for confirmation of alcohol related problems.

One such assay was and sold by the Addiction Research Foundation of Ontario is described in Canadian Patent No. 1,221,008. These assay strips as disclosed in Canadian Patent No. 1,221,008 provide very rapid and accurate determinations of blood alcohol levels. However, such assay strips are required to be manufactured using a lyophizing process. Such process restricts the product from being manufactured in batches of 10,000 strips. Further, these strips are stable at room temperature for only about 2 weeks and require to be maintained in a fridge or freezer to prevent loss of effectiveness.

SUMMARY OF THE INVENTION

The disadvantages of the prior art may be overcome by providing an inexpensive, quick and reliable means of determining accurately the alcohol concentration in a biological fluid which is suitable for manufacturing on a commercial scale and which is relatively stable at room temperature.

In accordance with one aspect of the invention, there is provided a composition for directly and rapidly determining the alcohol concentration of a lower alcohol in a biological fluid without dilution, comprising a substrate and a solid carrier bonded thereto. The carrier is impregnated with a solution having the following constituents mixed in effective amounts, a cross-linked stabilized enzyme for oxidizing said alcohol in the presence of a reducible compound to produce a corresponding aldehyde and a reduction product;

a chromogen which reacts with the reduction product in the presence of an agent to produce a coloured compound indicative of alcohol presence in the biological fluid;

a competitive inhibitor of the enzyme;

an agent for converting the chromogen to the coloured compound; and a buffer to maintain a predetermined acidic pH. The solution-impregnated carrier is dried in a hypobaric environment and can be stored at room temperature for extended periods of time with minimal loss of effectiveness.

In accordance with another aspect of the invention, the assay is produced in a dipstick format for dipping into a biological fluid and determining the alcohol content therein.

In accordance with another aspect of the invention, a method of manufacturing an assay for directly and rapidly determining the alcohol concentration of a lower alcohol in a biological fluid without dilution, comprising a solid carrier having a smooth side, said carrier being impregnated with a solution having the following constituents mixed in respective amounts:

a cross-linked stabilized enzyme for oxidizing said alcohol in the presence of a reducible compound to produce a corresponding aldehyde and a reduction product;

a chromogen which reacts with said reduction product in the presence of an agent to produce a coloured compound indicative of alcohol presence in said biological fluid;

a competitive inhibitor of said enzyme;

an agent for converting said chromogen to said coloured compound; and a buffer to maintain a predetermined acidic pH, the steps comprises:

running the carrier through the solution at a predetermined speed;

running the carrier through an air flow at the same speed;

laminating the carrier with the smooth side up;

maintaining the carrier in a vacuum chamber overnight to dry the solution onto the carrier;

cutting the carrier to a small pad;

affixing the pad to plastic sheets; and cutting the plastic sheets into dipsticks.

BRIEF DESCRIPTION OF THE DRAWINGS

Other and further advantages of the invention will be apparent to those skilled in the art from the following description, taken in conjunction with the following drawings, in which.

DETAILED DESCRIPTION OF THE INVENTION

Figure 1:
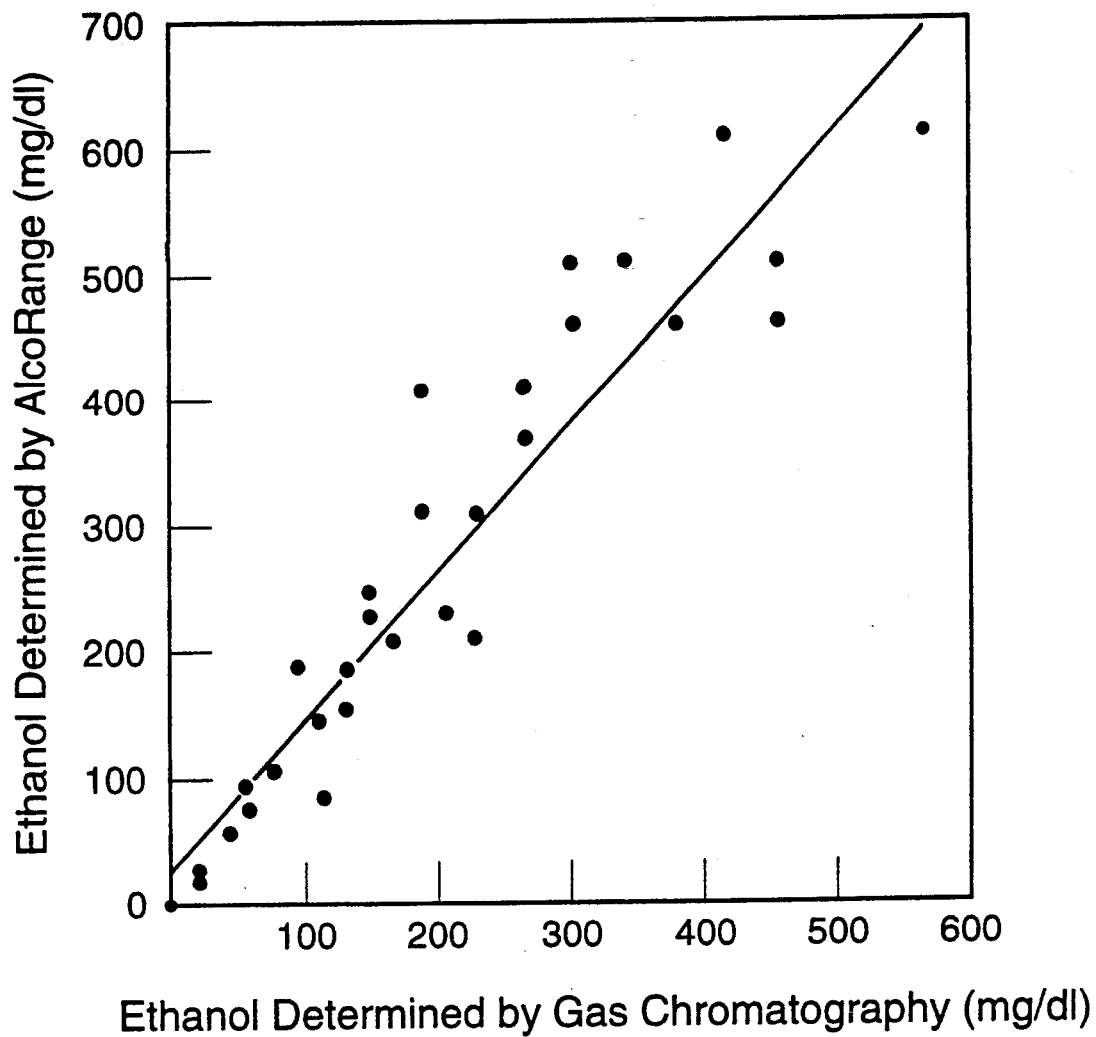
FIG. 1 is a graphic illustration of the correlation between the determination of the presence of ethanol in urine samples using the present invention by the inventors hereof and gas chromatography by laboratory personnel.

A cross-linked stabilized yeast alcohol dehydrogenase reacts, in the presence of pyrazole, a competitive inhibitor, with ethanol and nicotinamide adenine dinucleotide (NAD) to yield acetaldehyde plus NADH. NADH reduces iodonitrotetrazolium chloride (INT) in the presence of an excess of cross-linked stabilized diaphorase to yield reduced INT which presents an intense red colour.

Pyrazole in the reaction mixture increases the apparent Km for ethanol, such that the rate of NADH production, and thus the rate of colour development, are directionally proportional to the concentration of ethanol.

The result in colour is compared at a specific time against a calibrated scale ranging from green to red, representing alcohol concentrations of zero, 25, 50, 100, 200 and 400 mg/dl (0-0.4%; or 0-87 mmoles/l).

The sample volume which impregnates the reagent pad need not be controlled, thus allowing the determination of alcohol concentration in fluids of varied viscosity. When the reagent pad is wetted with an alcohol-containing solution, in a volume exceeding 10 $\mu$l, the pad changes colour from light green to greenish-grey and then to different intensities of red.

The reaction time required depends on whether the strips are used on freshly obtained clinical samples at 30° to 36° C. or on samples at varying room temperatures. In the latter case, the reaction time is determined by means of a single 100 mg/ml (0.1%) ethanol solution and water. To calibrate at a specific temperature, the reaction is allowed to proceed until the colour generated in the reagent pad matches the colour of the 100 mg/dl block. Such reaction time is recorded and it is further used for other samples at the same temperature.

Strips intended for determining ethanol concentration were prepared as follows. The stabilized enzyme diaphorase was prepared by cross-linking. A beaker containing 2,000 ml of pre-cooled phosphate buffered saline, pH 7.2 (PBS buffer) was kept on ice. With slow stirring, 20 grams diaphorase, having a specific activity 17 units/mg solid, and 120 grams bovine serum albumin (BSA) were completely dissolved in the buffer. 240 ml of pre-cooled 2.5% glutaraldehyde was then added within 15 minutes. Cross-linking was carried out at 4° C. with slow stirring for approximately 17 hours.

60 ml of pre-cooled 1 molar sodium cyanoborohydride (NaCNBH$_3$), with pH value adjusted to about pH 7.0, was added into the cross-linked enzyme solution to reduce the produced Schiff's base (>C=N-CR, where R is the amino acid residue). The mixture is then further stirred for two hours.

60 ml of pre-cooled 1 molar lysine with pH value adjusted to about pH 7, was then added into the beaker to stop the cross-linking reaction. The reaction mixture was kept on ice for another 3 hours.

After cross-linking, the solution was dispensed into a number of dialysis bags and dialysed against 100 liters of PBS at 4° C. The dialysis buffer was changed four times within 65 hours. The dialysed cross-linked enzyme can be stored at 4° C. or $-20$° C. before using.

If the specific activity of diaphorase is lower than 17 units/mg solid, the only change necessary is to increase the amount of diaphorase and reduce the amount of BSA to keep both the total activity of the enzyme and the total amount of proteins constant.

The stabilized enzyme alcohol dehydrogenase (ADH) is produced by cross-linking. ADH, having a specific activity 270 units/mg solid, was cross-linked with BSA in the presence of $1 \times 10^{-3}$ molar NAD and $1 \times 10^{-3}$ molar pyrazole. The procedure for ADH cross-linking was the same as for diaphorase, but the chemicals were different. For the cross-linking of 1.5 g ADH, the following chemicals were used; BSA, 9 g; NAD, 99.5 mg; pyrazole, 10.2 mg; PBS for cross-linking, 150 ml; 2.5% glutaraldehyde, 7.2 ml; 1 molar NaCNBH$_3$ (pH$\approx$7), 1.8 ml; 1 molar lysine (pH$\approx$7), 1.8 ml; PBS for dialysis, $5 \times 7.5$ liters.

| Formula of Solution | |
|---|---|
| a) NAD | $1.5 \times 10^{-2}$ M |
| b) mannitol | $3.0 \times 10^{-2}$ M |
| c) pyrazole | $7.0 \times 10^{-4}$ M |
| d) BRIJ-35 | 0.3% |
| e) potassium phosphate monobasic (KH$_2$PO$_4$) | $1.14 \times 10^{-1}$ M |
| f) dithioerythritol | $1.0 \times 10^{-5}$ M |
| g) ethylenediamine-tetraacetic acid, disodium salt (EDTA) | $1.0 \times 10^{-3}$ M |
| h) iodonitrotetrazolium violet | $3.0 \times 10^{-3}$ M |
| i) cross-linked diaphorase | 40,000 units/liter |
| j) cross-linked ADH | 100,000 units/liter |
| k) FD&C Blue #1 | 16 mg/liter |
| l) FD&C Yellow #5 | 25 mg/liter |
| m) FD&C Red #40 | 8 mg/liter |
| n) Final pH adjusted to 5.85 by adding 1 molar potassium hydroxide. | |

BRIJ-35 is the trademark of a surfactant polyoxyethylene-23-laurylether. Dithioerythritol is a sulphydryl containing compound used to protect the enzyme. The FD&C colours are available from Seeley & Co. Canada Ltd.

The competitive inhibitor in the preferred embodiment is pyrazole, but may be a halogenated pyrazole, methyl, ethyl, propyl, butyl or pentyl pyrazole or suitable steroid.

To manufacture the dipsticks using known technology and machinery for applying and coating chemicals to filter paper, the following steps are undertaken:

a) Clean the machinery with toluene one day before the manufacture day;

b) Keep the manufacture shop alcohol-free and 7% relative humidity;

c) Pour about 2 litres of the pre-cooled solution into a holding container on the machinery;

d) Run Whatman filter paper #3 through the solution at a speed of approximately 4 feet/minute;

e) Run the paper through a hot channel (33 feet in length) with air flow (CFM = 6.25 to 10.25, temperature = 55° C. to 66° C.) at the same speed.

f) Laminate the paper with the smooth side of the paper up;

g) Keep the paper roll in a hypobaric environment, namely, a vacuum chamber at approximately 27 inches Hg at a temperature of between 55° C. to 66° C., overnight to dry the solution onto the paper;

h) Cut the paper to approximately small pads and affix to plastic sheets to be cut to make dipsticks;

i) Put the dipsticks in bottles and store them at 4° C.

Those skilled in the art will recognize that the sensitivity of the detection of different alcohol levels can be varied depending on the specific application desired by altering the relative concentrations of pyrazole and ADH without departing from the spirit of this invention.

A semipermeable coating may also be provided over the paper pad to permit smaller molecules such as alcohol to pass therethrough and react with the impregnate and to prevent red cells and larger molecules such as proteins and haemoglobin from passing through.

The pad may also be coated to enhance optical qualities of the final colour formed.

A dipstick type assay has been disclosed. However, it is apparent to those skilled in the art that the carrier of the solution may be an inert powder material such as silica gel, kiesel-guhr or microcrystalline cellulose. The inert powder may be compounded with active ingredients and compressed using known methods into a tablet form or may be placed in an opened ended tube depending on the circumstances.

In use, a dipstick is prepared in accordance of the invention and prepared according to the foregoing example. The dipstick is dipped for 1 to 2 seconds in the fluid suspected of containing ethanol. The intensity of the pink to red colour that develops in the active end of the dipstick is proportional to the concentration of alcohol present in the fluid. After the calibrated period of time, the colour of the dipstick is compared to a colour chart and the concentration of the alcohol in the fluid can be determined.

When using the reagent strip, the clinician should not touch the reagent pad of the strip with his or her fingers. The excess fluid may be removed by briefly touching the edge of the strip against a blotting pad without affecting the reagent area. The colour matching must be performed at the proper time. The method requires that the production proceed for a specific calibrated time.

Alcohol reagent strips made according to the present invention were tested with different types of samples. First, ethanol was diluted in distilled water to the concentrations desired and secondly laboratory urine and saliva samples of laboratory personnel and students at the University of Toronto, who had not consumed alcohol in the past 24 hours were adjusted to specific ethanol concentration by adding concentrated alcohol. The dilution or saliva samples did not exceed 5%. These samples were used to assess the accuracy of the colour scale of the present invention and to determine whether there was concordance in reaction time between urine, saliva and water samples. Some samples were purposely adjusted to higher alcohol levels that could be read by the colour scale.

FIG. 1 illustrates the results of estimates alcohol concentration in saliva samples from control individuals with added varying amounts of alcohol against the ethanol levels determined from gas chromatography by laboratory personnel. The two methods correlate highly at $r=0.96$, $p<0.001$ and slope=1.16.

The time require for colour matching to the respective colour block was virtually identical for all concentrations in the range. 25 to 27 seconds was required to match the colour of their reagent pad with the colour scale. Table 1 shows a result that the time required for matching to the colour scale was virtually identical for water, urine or saliva samples.

TABLE 1

| | Time Required for Colour Matching in the Complete Concentration Range (25 to 400 mg/dl) | | |
|---|---|---|---|
| | Ethanol/water | Ethanol/urine | Ethanol/saliva |
| 1. | 20.4" ± 1.3 | 23.6" ± 0.9 | 22.6" ± 0.7 |
| 2. | 28.4" ± 1.8 | 39.6" ± 1.5 | 28.4" ± 3.2 |
| 3. | 21.0" ± 1.0 | 20.0" ± 1.3 | 17.8" ± 0.5 |
| 4. | 22.2" ± 0.8 | — | — |
| 5. | 24.8" ± 0.4 | 24.4" ± 1.5 | 26.4" ± 0.5 |
| 6. | 30.2" ± 0.8 | 28.2" ± 1.4 | 28.0" ± 0.8 |
| 7. | 27.2" ± 1.6 | 25.6" ± 1.6 | 24.2" ± 1.6 |
| 8. | 26.0" ± 0.5 | 21.2" ± 1.4 | 26.2" ± 1.6 |
| 9. | 36.4" ± 0.5 | 34.8" ± 0.4 | 29.2" ± 0.9 |
| Average | 26.3" ± 1.7 | 27.2" ± 2.4 | 25.4" ± 1.3 |

Average time required for colour matching of ethanol/water samples by 9 non-experienced users: 25 mg/dl (27.4" ± 2.2); 50 mg/dl (27.1" ± 1.4); 100 mg/dl (25.8" ± 1.9); 200 mg/dl (25.1" ± 1.7); 400 mg/dl (26.0 ± 1.9)

In a first series of a clinical study, urine and plasma samples were obtained from patients at the emergency room of three Toronto teaching hospitals where the main reason for consulation or admission of the patient was alcohol related. The samples were kept frozen. Before analysis, the samples were allowed to warm up to room temperature (22°-23° C.) and the reaction time was determined according to the calibration mode as discussed previously. The alcohol level in the urine and serum samples was analyzed by gas chromatography.

Figure 2:
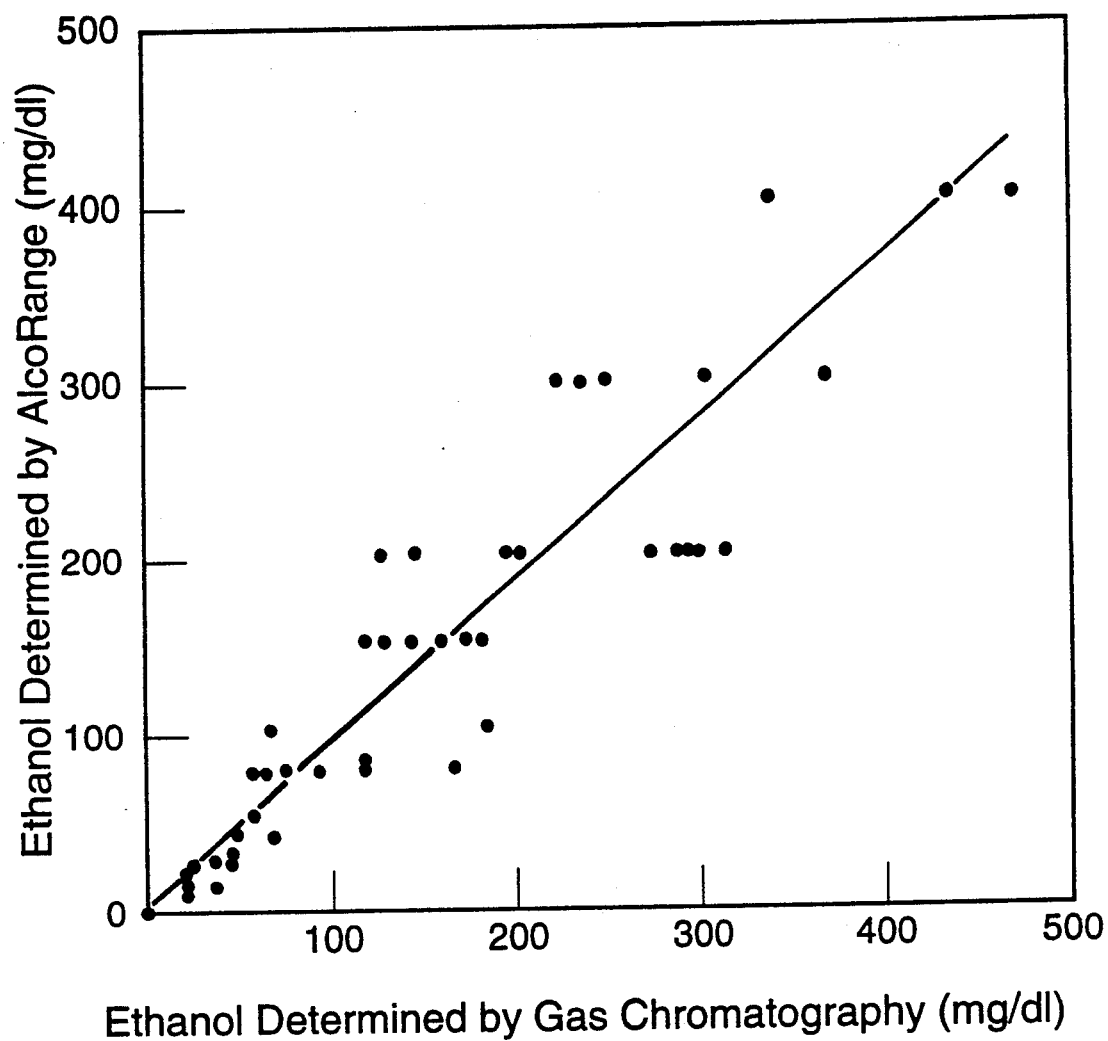
FIG. 2 is a graphic illustration of the correlation between the determination of the presence of ethanol in urine samples using the present invention by non-experienced individuals and gas chromatography by laboratory personnel.

The alcohol levels in the clinical urine samples were estimated by gas chromatography by laboratory personnel and by using the alcohol reagent strip according to the present invention by 10 non-experienced individuals. FIG. 2 provides an example of 1 of 10 users where the correlation between the two results has a correlation factor of 0.93. Table 2 lists the correlation coefficients and slopes for each of the 10 non-experienced users. The two methods, gas chromatography and the alcohol reagents strips showed a good correlation with a mean r value of 0.92±0.02, a p value less than 0.001 with a slope of 0.97±0.14.

TABLE 2

| | Correlations between new ALCORANGE and Gas Chromatography Methods for the Ethanol Concentration Determination in 54 Clinical Urine Samples by 10 Non-Experienced Dipstick Users | |
|---|---|---|
| | Correlation Coefficient | Slope |
| 1. | 0.9478 | 1.0295 |
| 2. | 0.9334 | 0.9255 |
| 3. | 0.9442 | 0.8220 |
| 4. | 0.8823 | 0.8090 |
| 5. | 0.9394 | 0.9861 |
| 6. | 0.9200 | 1.1318 |
| 7. | 0.8930 | 1.2144 |
| 8. | 0.9144 | 0.9995 |
| 9. | 0.9072 | 0.7987 |
| 10. | 0.9138 | 1.0158 |
| Mean ± SD | 0.92 ± 0.02 | 0.97 ± 0.14 |

Figure 3:
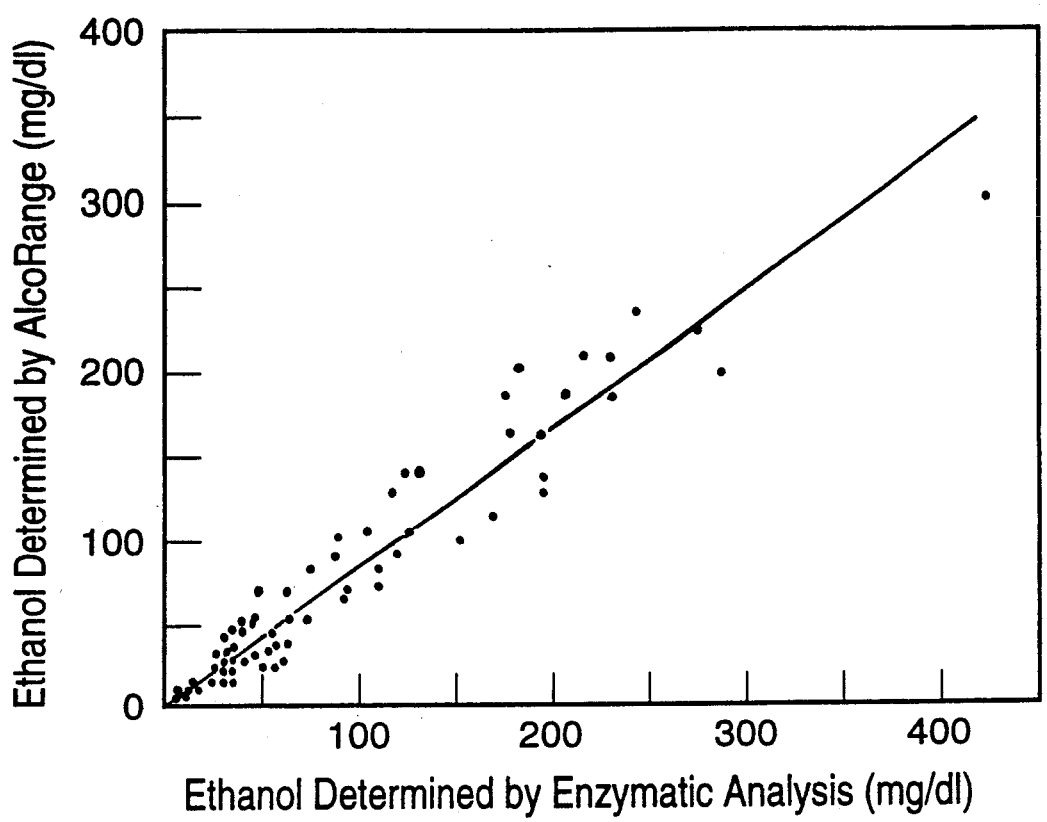
FIG. 3 is a graphic illustration of the correlation between the determination of the presence of ethanol in urine samples using the present invention by non-experienced individuals having 10–15 minutes of training and enzymatic analysis by laboratory personnel.

Urine samples were also analyzed for alcohol by an automated alcohol dehydrogenase method and kept refrigerated at a temperature of 4° C. for one week before being analyzed by the reagent strips of the present invention. The two methods showed a high correlation of $r=0.97$, $p<0.001$ at a slope of 0.83, (See FIG. 3).

Figure 4:
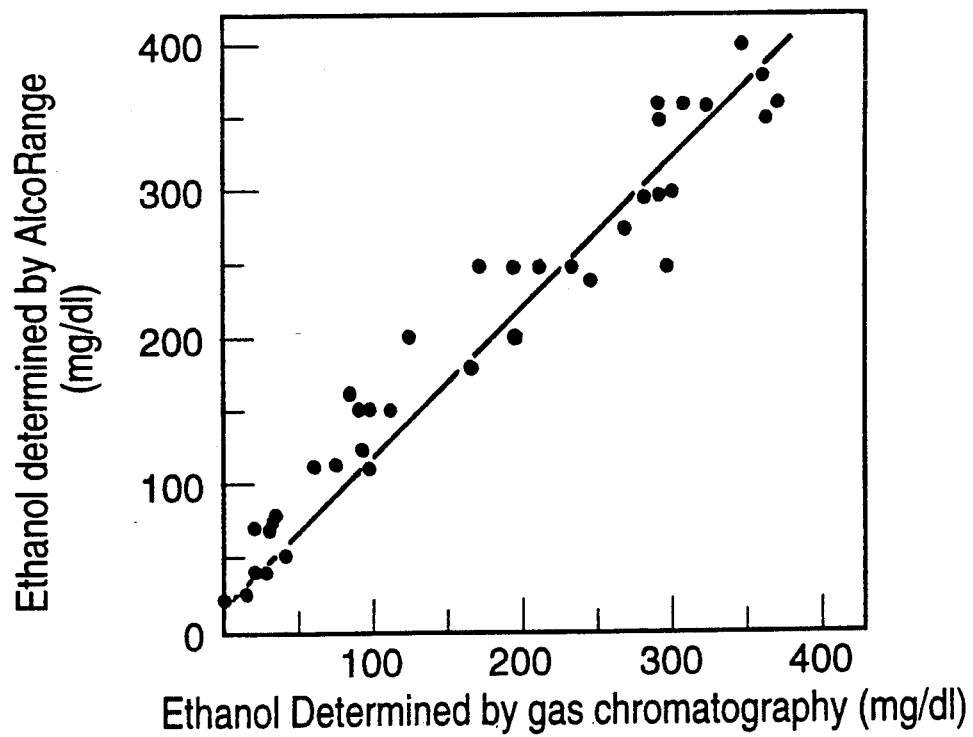
FIG. 4 is a graphic illustration of the correlation between the determination of the presence of ethanol in plasma samples using the present invention by one of the inventors, who was blind with respect to the concentration of ethanol in the samples and gas chromatography by laboratory personnel.

Plasma samples were prepared and the alcohol content thereof was determined by gas chromatography by laboratory personnel. Strips of the present invention was also used to determine the alcohol content. The two methods showed a high correlation of r=0.98, p<0.001 at a slope of 1.10, (See FIG. 4).

In the second series of the clinical study, sera were prepared from blood samples from twelve teaching and community hospitals for alcohol or drug analysis.

Figure 5:
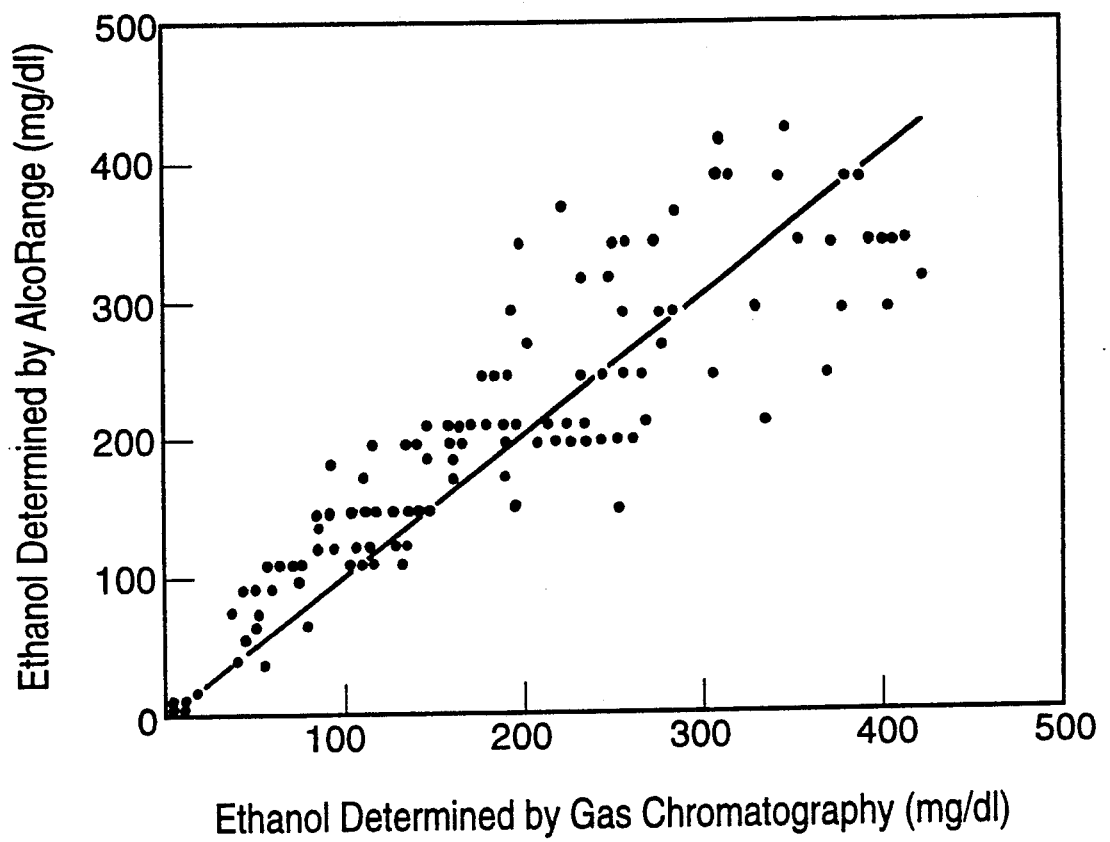
FIG. 5 is a graphic illustration of the correlation between the determination of the presence of ethanol in serum samples using the present invention by one of the inventors, who was blind with respect to the concentration of ethanol in the samples and gas chromatography by laboratory personnel.

Alcohol levels were determined blindly by gas chromatography and by the reagent strips according to the present invention. The two methods showed a high correlation of r=0.98, p<0.001 at a slope of 0.92 (FIG. 5).

Methanol, isopropanol and ethylene glycol laboratory samples were prepared in water at seven different concentrations and tested with the reagent strips of the present invention. All samples containing methanol, isopropanol and ethylene glycol yielded negative results by the reagent strips of the present invention.

The stability of the reagent strips of the present invention was tested at different temperatures for up to four months. During this period, the container housing the reagent strips was opened a maximum of 25 times to remove one strip each time and then recapped. This was done in 100% humidity atmosphere at each temperature. Although the time required to remove one strip is approximately 3–5 seconds, the container was allowed to remain open for a total of 10 seconds. When the reagent strip container was kept for stability studies at 4° C., the bottle was opened at 30° C., 100% humidity without a warming up period. However, after removing the reagent strip, it was allowed to attain room temperature for about 30–45 seconds. Moving of the reagent strip in the air while holding it was done at time to rapidly bring the strips to room temperature.

As with any enzymatic reaction, temperature affects the reaction rate. Reaction times required for 22°, 27°, 32° and 36° C. were 26, 15, 12 and 11 seconds respectively. Thus when the sample temperature increased from 22° to 32° C., the reaction time was decreased by 53%. In the range of freshly obtained clinical samples (32°–36° C.) the reaction time was found to vary only 9%.

The reagent strip is considered to be stable if its activity following storage exceeded 90% of the original activity. In other words, a maximum of 10% loss is permitted.

The storage stability of the reagent strip of the present invention has been found to be temperature dependent as illustrated in Table 3. The reagent strip is estimated to be stable for up to $2.12 \times 10^4$ days at 4° C. (approximately 58 years). If stored at room temperature (22°–23° C.), the reagent strip of the present invention is stable for up to $1.1 \times 10^2$ days (3–4 months). However, if the reagent strip is stored at 30° C., 10% of its activity is lost in 18 days.

TABLE 3

| Storage Stability of new ALCORANGE | |
|---|---|
| Storage Temperature (°C.) | t 0.1 (days) |
| 4 | $2 \times 10^{4}$* |
| 23 | 110 |
| 25 | 68* |
| 30 | 18 |
| 37 | 7 | t 0.1: Days for 10% loss in the reagent activity
*Calculated according to Arrhenius equation: $\log t''_{0.1} = \log t'_{0.1} + \text{slope} \times (1/T'' - 1/T')$ where T' and T'' are absolute temperature, slope is $9.85 \times 10^3$ obtained from the Arrhenius plot of the data determined at 23 and 30° C.

Although the preferred embodiment of the present invention has been illustrated and described, it will be apparent to those skilled in the art that various changes and modification may be made without departing from the spirit and scope of the invention.

We claim:

1. A composition for directly and rapidly determining the alcohol concentration of a lower alcohol in a biological fluid without dilution, comprising a solid carrier impregnated with a solution having the following constituents mixed in effective amounts:

a cross-linked and stabilized alcohol dehydrogenase for oxidizing said alcohol in the presence of nicotinamide adenine dinucleotide to produce a corresponding aldehyde and a reduction product, wherein said alcohol dehydrogenase is stabilized and cross-linked using bovine serum albumin and glutaraldehyde;

a competitive inhibitor of alcohol dehydrogenase;

a cross-linked and stabilized diaphorase for converting said chromogen to said coloured compound, wherein said diaphorase is stabilized and cross-linked with bovine serum albumin and glutaraldehyde;

a chromogen which reacts with said reduction product in the presence of diaphorase to produce a coloured compound indicative of alcohol presence in said biological fluid;

a buffer to maintain said solution at a predetermined acidic pH.

2. A composition as claimed in claim 1 wherein said alcohol dehydrogenase and said diaphorase are stabilized and cross-linked in phosphate buffered saline.

3. A composition as claimed in claim 2 wherein said composition further includes mannitol.

4. A composition as claimed in claim 3 wherein said solution-impregnated carrier is dried in a hypobaric environment at between 55° to 66° C.

5. A composition as claimed in claim 2 wherein said competitive inhibitor is selected from a group consisting of a pyrazole, a halogenated pyrazole, an alkyl pyrazole and a steroid.

6. A composition as claimed in claim 5 wherein said chromogen is a tetrazolium salt including iodonitrotetrazolium chloride.

7. A composition as claimed in claim 6 wherein said solution further includes a reductor to protect said enzyme.

8. A composition as claimed in claim 7 wherein said reductor is dithioerythritol.

9. A composition as claimed in claim 6 wherein said composition maintains 90% of its activity for about 3 to 4 months when stored at room temperature.

10. A composition as claimed in claim 6 wherein said composition maintains 90% of its activity for about $2.12 \times 10^4$ days when stored at 4° C.

11. A composition for directly and rapidly determining the alcohol concentration of a lower alcohol in a biological fluid without dilution, comprising a solid carrier impregnated with a solution having the following constituents mixed in respective amounts:

| nicotinamide adenine dinucleotide | $1.5 \times 10^{-2}$ M |
|---|---|
| mannitol | $3.0 \times 10^{-2}$ M |
| pyrazole | $7.0 \times 10^{-4}$ M |
| polyoxy-ethylene-23-laurylether | 0.3% |
| $KH_2PO_4$ | $1.14 \times 10^{-1}$ M |
| dithioerythritol | $1.0 \times 10^{-5}$ M |
| EDTA | $1.0 \times 10^{-3}$ M |
| iodonitrotetrazolium violet | $3.0 \times 10^{-3}$ M |

| | |
|---|---|
| cross-linked diaphorase | 40,000 units/liter |
| cross-linked alcohol dehydrogenase | 100,000 units/liter |
| FD&C Blue #1 | 16 mg/liter |
| FD&C Yellow #5 | 25 mg/liter |
| FD&C Red #40 | 8 mg/liter, | said solution having a pH adjusted to about 5.85, wherein said cross-linked diaphorase and said cross-linked alcohol dehydrogenase are cross-linked in phosphate buffered saline using bovine serum albumin and glutaraldehyde producing Schiff's bases, and subsequently reducing said Schiff's bases with sodium cyanoborohydride and terminating cross-linking with lysine and wherein said cross-linked diaphorase and said cross-linked alcohol dehydrogenase are dialysized against phosphate buffered saline.

* * * * *